United States Patent
Chang

(10) Patent No.: US 9,572,528 B1
(45) Date of Patent: Feb. 21, 2017

(54) MONITOR FOR SIDS RESEARCH AND PREVENTION

(71) Applicant: Los Angeles Biomedical Research Institute at Harbor-UCLA Medical Center, Torrance, CA (US)

(72) Inventor: Ruey-Kang Chang, Diamond Bar, CA (US)

(73) Assignee: Los Angeles Biomedical Research Insitute at Harbor-UCLA Medical Center, Torrance, CA (US)

( * ) Notice: Subject to any disclaimer, the term of this patent is extended or adjusted under 35 U.S.C. 154(b) by 572 days.

(21) Appl. No.: 13/957,308

(22) Filed: Aug. 1, 2013

Related U.S. Application Data

(60) Provisional application No. 61/680,205, filed on Aug. 6, 2012.

(51) Int. Cl.
*A61B 5/00* (2006.01)

(52) U.S. Cl.
CPC ........... *A61B 5/4818* (2013.01); *A61B 5/4806* (2013.01); *A61B 2503/04* (2013.01)

(58) Field of Classification Search
None
See application file for complete search history.

(56) References Cited

U.S. PATENT DOCUMENTS

| | | | |
|---|---|---|---|
| 4,440,177 A | 4/1984 | Anderson et al. | |
| 4,494,553 A | 1/1985 | Sciarra et al. | |
| 4,639,455 A | 1/1987 | Moore | |
| 4,696,307 A | 9/1987 | Montgieux | |
| 4,696,517 A | 9/1987 | Nagano | |
| 4,700,697 A | 10/1987 | Mundell et al. | |
| 4,738,266 A | 4/1988 | Thatcher | |
| 4,851,816 A | 7/1989 | Macias et al. | |
| 4,862,144 A | 8/1989 | Tao | |

(Continued)

OTHER PUBLICATIONS

Exmovere Holdings, Inc., "With an Eye to New Moms, Exmovere Unveils Biosensor Pajamas for Babies", http://globenewswire.com/newsroom/news.html?d=200247, (Aug. 27, 2010).

(Continued)

*Primary Examiner* — Gary Jackson
*Assistant Examiner* — Nathan A Baldwin
(74) *Attorney, Agent, or Firm* — K&L Gates LLP; Louis C. Cullman; Brian J. Novak

(57) ABSTRACT

A system including a monitoring device dimensioned for placement on a human. The monitoring device including a plurality of sensors for monitoring a sleep position, a temperature, a carbon dioxide level and a respiration of the human. The system further including a processing unit coupled to the monitoring device, the processing unit capable of processing information from the plurality of sensors and performing an algorithm to determine the presence of a sudden infant death syndrome (SIDS) risk factor based on the information. A method may include monitoring two or more of a sleep position, a respiration, a temperature and a carbon dioxide level of a subject. An algorithm may be automatically performed based on the monitoring, to determine the presence of a SIDS risk factor. The results of the algorithm may be displayed and an alert can be sent to, for example, a mobile device based on the risk level.

19 Claims, 8 Drawing Sheets

(56) References Cited

U.S. PATENT DOCUMENTS

| | | | |
|---|---|---|---|
| 4,969,451 A | 11/1990 | Totten | |
| 4,985,444 A | 1/1991 | Shiokawa et al. | |
| 5,105,354 A | 4/1992 | Nishimura | |
| 5,131,412 A | 7/1992 | Rankin | |
| 5,234,930 A | 8/1993 | Shiokawa et al. | |
| 5,241,300 A | 8/1993 | Buschmann | |
| 5,303,699 A | 4/1994 | Bonassa et al. | |
| 5,305,483 A | 4/1994 | Watkins | |
| 5,317,767 A | 6/1994 | Hargest et al. | |
| 5,366,271 A | 11/1994 | Johnston et al. | |
| 5,389,037 A | 2/1995 | Hale | |
| 5,454,376 A | 10/1995 | Stephens et al. | |
| 5,483,711 A | 1/1996 | Hargest et al. | |
| 5,498,423 A | 3/1996 | Zisapel | |
| 5,500,225 A | 3/1996 | Laudon et al. | |
| 5,505,199 A | 4/1996 | Kim | |
| 5,515,865 A | 5/1996 | Scanlon | |
| 5,556,759 A | 9/1996 | Beach | |
| 5,615,688 A | 4/1997 | O'Dwyer | |
| 5,675,852 A | 10/1997 | Watkins | |
| 5,684,460 A | 11/1997 | Scanlon | |
| 5,686,491 A | 11/1997 | Sherwood | |
| 5,747,266 A | 5/1998 | Beach | |
| 5,787,534 A | 8/1998 | Hargest et al. | |
| 5,796,340 A | 8/1998 | Miller | |
| 5,819,741 A | 10/1998 | Karlsson et al. | |
| 5,857,232 A | 1/1999 | Mahdavi | |
| 5,914,660 A | 6/1999 | Mesibov et al. | |
| 5,968,918 A | 10/1999 | Kanda | |
| 6,011,477 A * | 1/2000 | Teodorescu | A61B 5/113 340/573.1 |
| 6,023,802 A | 2/2000 | King | |
| 6,036,263 A | 3/2000 | Gold | |
| 6,047,201 A | 4/2000 | Jackson, III | |
| 6,052,849 A | 4/2000 | Dixon et al. | |
| 6,055,690 A | 5/2000 | Koenig | |
| 6,083,756 A | 7/2000 | Hedner et al. | |
| 6,208,897 B1 | 3/2001 | Jorgenson et al. | |
| 6,333,055 B1 | 12/2001 | Wiklund | |
| 6,375,621 B1 | 4/2002 | Sullivan | |
| 6,438,775 B1 | 8/2002 | Koenig | |
| 6,492,634 B2 | 12/2002 | Marchitto et al. | |
| 6,553,256 B1 | 4/2003 | Jorgenson et al. | |
| 6,553,589 B1 | 4/2003 | Hartman | |
| 6,684,437 B2 | 2/2004 | Koenig | |
| 6,897,773 B2 | 5/2005 | Ridley | |
| 6,956,175 B1 | 10/2005 | Daly et al. | |
| 7,035,432 B2 | 4/2006 | Szuba | |
| 7,037,272 B2 | 5/2006 | Silpachai et al. | |
| 7,101,554 B2 | 9/2006 | Niklasson | |
| 7,197,358 B2 | 3/2007 | Haghighi-Mood et al. | |
| 7,305,262 B2 | 12/2007 | Brodnick et al. | |
| 7,374,753 B1 | 5/2008 | Farmer et al. | |
| 7,442,380 B2 | 10/2008 | Niklasson | |
| 7,593,764 B2 | 9/2009 | Kohls et al. | |
| 7,704,990 B2 | 4/2010 | Landry et al. | |
| 7,801,591 B1 * | 9/2010 | Shusterman | A61B 5/0205 600/300 |
| 7,855,277 B2 | 12/2010 | Niklasson | |
| 7,862,115 B1 | 1/2011 | Davis | |
| 7,961,093 B2 * | 6/2011 | Chiao | A61B 5/0002 340/539.12 |
| 8,013,003 B2 | 9/2011 | Street et al. | |
| 2006/0155205 A1 * | 7/2006 | Sotos | A61B 5/4806 600/529 |
| 2009/0163778 A1 * | 6/2009 | Sommerville | G08B 21/0208 600/301 |
| 2010/0217158 A1 * | 8/2010 | Wolfe | A61B 5/113 600/595 |
| 2010/0274104 A1 * | 10/2010 | Khan | A61B 5/02055 600/301 |
| 2012/0083670 A1 * | 4/2012 | Rotondo | A61B 5/1116 600/301 |

OTHER PUBLICATIONS

Kaminski, Joseph, "Baby Tech: Angel Care Movement Sensor with Sound Monitor", http:news.cnet.com/8301-17938_105-10027433-1.html, (Aug. 27, 2008).

Patel et al., Inspired $CO_2$ and $O_2$ in sleeping infants rebreathing from bedding: relevance for sudden infant death syndrome. J. Appl. Phsyiol., 91: 2537-2454 (2001).

Djupesland et al., Computational simulation of accumulation of expired air in the infant cot. Acta Otolaryngol, Supp 543: 183-185 (2000).

* cited by examiner

MONITOR FOR SIDS RESEARCH AND PREVENTION

CROSS-REFERENCE TO RELATED APPLICATION

This application claims priority from U.S. Provisional Patent Application Ser. No. 61/680,205, filed on Aug. 6, 2012.

FIELD

Device, system and methods for local and remote monitoring infants, and algorithms for assessing an infant's sleep environment. In particular, device, system and methods for detecting sudden infant death syndrome (SIDS) risk factors.

BACKGROUND

Sudden infant death syndrome (SIDS) is one of the most mysterious disorders in medicine. While the pathophysiologic mechanisms of SIDS are not fully understood, many key environmental risk factors for SIDS are known. The most important discovery has been that the prone sleep position triples the risk for SIDS. This discovery led to the national Back to Sleep campaign in 1994 and, a dramatic, 58% decrease in SIDS incidence. Because SIDS commonly occurs in apparently healthy infants, effective interventions for SIDS will have impact on all 4.1 million infants born in the U.S. each year.

Although the Back to Sleep campaign had tremendous initial success, SIDS is still the leading cause of infant death beyond the first month of life, and its incidence has not changed since 2000. Scientific and public health communities now face two critical barriers: (1) the roles of environmental risk factors in mechanisms leading to SIDS remain unclear (i.e., why does Back To Sleep work?); and (2) despite substantial resources devoted to educating the public, >30% of U.S. infants (1.2 million) do not sleep in the recommended supine position.

Apnea monitors have been used in infants for over 30 years. However, these monitors of cardiorespiratory parameters have not prevented SIDS because they target the wrong parameters. Furthermore, changes in physiologic parameters are hard to recognize by parents and often occur too late for intervention. These monitors focused on only the physiologic parameters of the infant but not the important environmental risk factors and how the infant responds to the environmental changes. Thus, SIDS research and prevention has encountered major obstacles and SIDS remains the leading cause of death for infants over 1 month of age.

BRIEF DESCRIPTION OF THE DRAWINGS

The following illustration is by way of example and not by way of limitation in the figures of the accompanying drawings in which like references indicate like elements. It should be noted that references to "an" or "one" embodiment in this disclosure are not necessarily to the same embodiment, and such references mean at least one.

DETAILED DESCRIPTION

Figure 1:
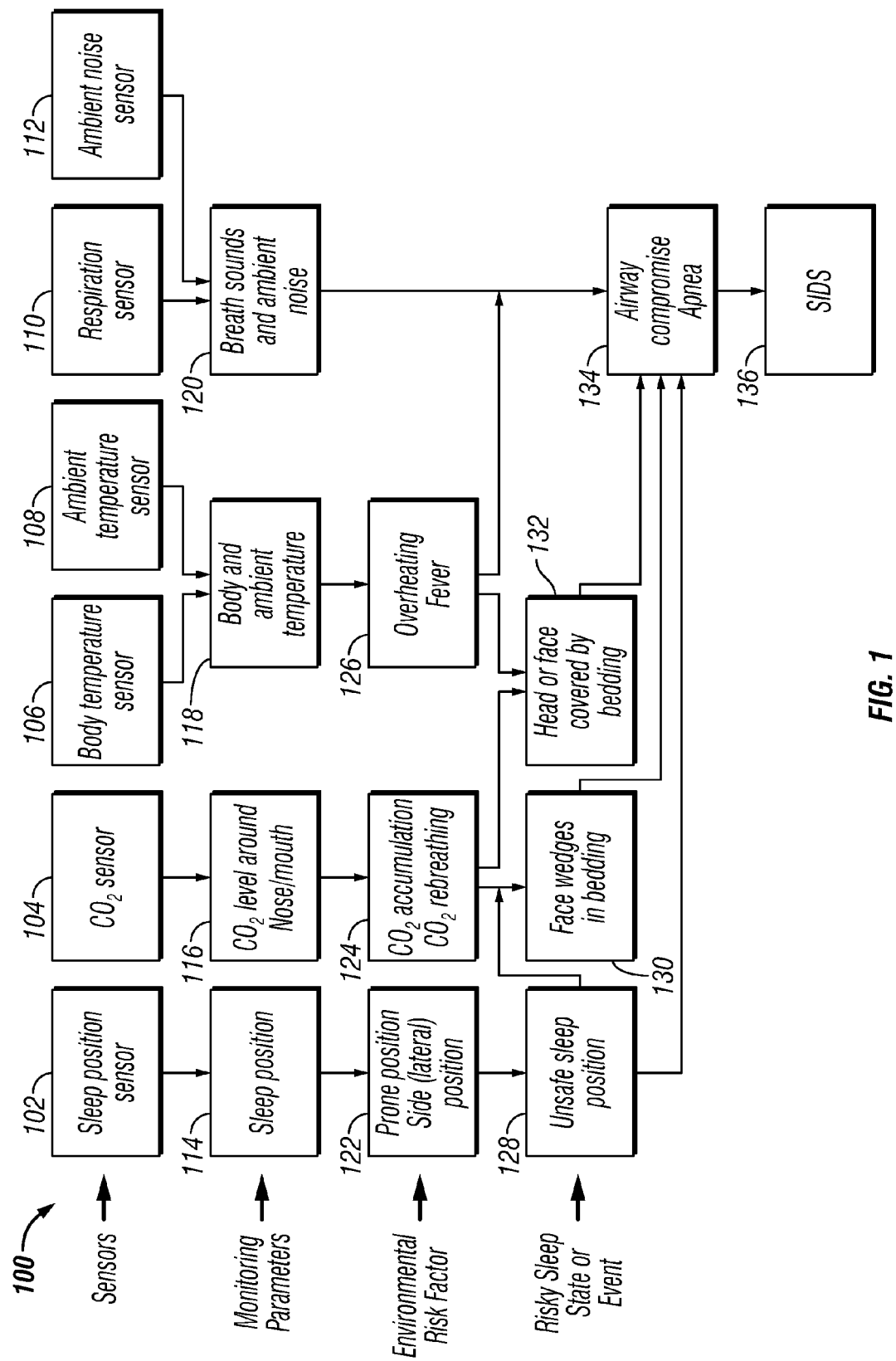
FIG. 1 is a block diagram illustrating sensors implemented within an infant monitoring device to detect the parameters of an infant's sleep environment and an algorithm to determine the state of an infant's sleep and the emergence of environmental risk factors for SIDS.

In this section we shall explain several preferred embodiments of this invention with reference to the appended drawings. Whenever the shapes, relative positions and other aspects of the parts described in the embodiments are not clearly defined, the scope of the invention is not limited only to the parts shown, which are meant merely for the purpose of illustration. Also, while numerous details are set forth, it is understood that some embodiments of the invention may be practiced without these details. In other instances, well-known structures and techniques have not been shown in detail so as not to obscure the understanding of this description.

A method, device and system for local and remote monitoring of environmental risk factors for SIDS is described herein. In one aspect, the device, system and method may be used to monitor for SIDS risk factors in newborns and infants. The term "newborn" generally refers to babies less than one month old, and "infants" refers to babies under 12 months old. The method and device described herein may be used to monitor a sleep environment of newborns and infants and therefore may be used at home by a parent or other infant care provider for monitoring on a daily basis. Representatively, the sleep environment and infant may be monitored simultaneously for SIDS risk factors, and based on such monitoring, a diagnostic algorithm may be applied to detect a risky sleep state of an infant and determine a risk level for SIDS occurrence.

The system therefore offers an approach to infant sleep monitoring, in which both the infant and the infant's sleep environment are monitored in order to detect modifiable environmental risk factors for SIDS. Among the modifiable environmental risk factors for SIDS, sleep position and head covering by bedding are the two most prevalent and important factors that can compromise an infant's airway and breathing. Unsafe sleep position and head covering by bedding are also the most easily correctable risk factors that can be identified and intervened in time to avoid further deterioration that leads to SIDS. Research has shown that SIDS rarely occurs in infants who are in the supine position without the head covered. By keeping infants in the supine sleep position and avoiding head covering during the critical developmental period, it is believed based on medical literature that SIDS incidence can be reduced by 70% or more. Proposed mechanisms of death due to head covering include $CO_2$ at rebreathing and heat stress, which may lead to decreased arousal and apnea. It has been suggested that avoiding head covering can reduce SIDS deaths by 27%. Thus, it is believed that by monitoring $CO_2$ levels along with the temperature of the infant, as is provided by embodiments disclosed herein, clinically significant head covering episodes can be detected and a care provider alerted before SIDS occurs. This information in combination with monitoring of risk factors of non-supine sleep position and abnormal breathing will be important for care providers to identify risky sleep states of infants so that appropriate interventions can be taken in time to prevent SIDS.

To detect an infant's risky sleep environment of non-supine sleep position and head covering by bedding, which could compromise airway and breathing, a method and infant monitoring device using sensors to monitor the infant and the infant's sleep environment conditions are used. These sensors include a sleep position sensor, a temperature sensor, a carbon dioxide sensor for head covering episodes leading to overheating and carbon dioxide ($CO_2$) accumulation, and a respiration sensor to detect the airway flow. In one embodiment, the device includes an accelerometer for monitoring sleep position, a temperature sensor, a carbon dioxide sensor and microphone to detect abnormal breathing. In some embodiments, the infant monitoring device may include two temperature sensors, one to monitor the infant's temperature and one to monitor a temperature of the environment. The infant monitoring device may further include an ambient noise sensor such as a microphone to monitor environmental noises. The signal data detected by the microphone serving as the ambient noise sensor may be subtracted from the signal data detected by the microphone of the respiration sensor to eliminate any ambient noise signals from the infant breathing sound signals.

The infant sleep environment monitoring device may be part of a monitoring system which includes a gateway at crib-side, and a remote monitoring server. The gateway receives sensor input from the infant monitoring device, processes the signals based on built-in diagnostic algorithms, generates management recommendations or alarms for care providers, and sends the data to a remote monitoring server. As will be described below, the integration of these sensors into a single device with algorithms for sensor input processing can significantly improve detection of a risky sleep environment prevent and help to prevent the occurrence of SIDS.

In one embodiment, the monitoring device includes a first portion and a second portion that form compartments for containing the sensors, and a bridge connecting the first and second portions. The first portion can be positioned on the infant so as to contact a region of the skin at the suprasternal notch or upper chest area. The first portion of the monitoring device can be dimensioned to contain sensors that should be positioned near the suprasternal notch. Representatively, the first portion can contain the sleep position sensor, body temperature sensor, respiration sensor (e.g. a microphone) and a microcontroller unit (MCU) with an integrated radiofrequency (RF) transceiver. The second portion may be dimensioned to contain all the other components of the device. Such components may include, for example, the carbon dioxide ($CO_2$) sensor, an ambient temperature sensor, an ambient noise sensor such as a microphone, a MCU with an integrated radiofrequency (RF) transceiver, wireless transmitter, flash memory, voltage regulator and a battery. Data from each of these sensors may be transferred to a crib side gateway device and analyzed using the diagnostic algorithm to determine the presence of SIDS risk factors. When the presence of SIDS risk factors is determined, the monitoring device or the crib side gateway may alert the care provider, for example by sounding an alarm at a local alarm device or at personal mobile devices. The diagnostic results may further be used to determine management recommendations for a care provider. The management recommendations may be displayed on a display such as a liquid crystal display (LCD) touch screen of, for example, the gateway. The device may be operated in a healthcare setting by, for example, nurses, physicians, and/or nurse's assistants, at the infant's home by the parent or other care provider, or at an infant day care center.

In another embodiment, the monitoring device includes one compartment that contains all the sensors, MCU, battery and all other components.

The monitoring device will be placed on the infant's suprasternal notch to upper chest area. Sensors including the temperature sensor and respiration sensor will be located in the undersurface of the device so that they have adequate skin contact in order to provide adequate sensing of the infant's skin temperature and airway sounds. Sensors including an ambient noise sensor, ambient temperature sensor and $CO_2$ sensor will be located at the upper surface of the device so that they are exposed to ambient sounds, temperature and $CO_2$ level for adequate sensing of the environment.

In one aspect, it is believed that a multi-sensor integrated device as described herein will improve clinical care for newborns and infants, revitalize public health efforts to reduce SIDS, and advance scientific research in SIDS and sleep medicine. In particular, by monitoring risk factors such as temperature and $CO_2$ at the same time, researchers will gain valuable data on how thermal stress and $CO_2$ rebreathing occur when a newborn or infant changes position or the head becomes covered. Moreover, the device will allow for evaluation of how these risk factors interact with each other to produce apnea and/or SIDS. In addition, the device includes a wireless transmission platform for real-time—onsite and central—monitoring of the sleep states of a large number of infants simultaneously. The platform is suitable for large-scale deployment, due to the ease of use, low cost, familiar consumer technology and interfacing, and data collection at a central, secure server. The platform may also be useful in pharmaceutical studies and vaccine trials in children who are monitored for adverse reactions at home, as well as in sleep research.

FIG. 1 is a block diagram illustrating the sensors that may be integrated within the monitoring device to detect the parameters of an infant's sleep environment and an algorithm to determine the state of an infant's sleep and the emergence of environmental risk factors for SIDS. In one embodiment, infant monitoring device may include a sleep position sensor 102, a $CO_2$ sensor 104, a body temperature sensor 106, an ambient temperature sensor 108, a respiration sensor 110 and an ambient noise sensor 112. Each of the sensors may be used to monitor various parameters of the infant and environment surrounding the infant.

Representatively, the sleep position sensor 102 may, in some embodiments, be an accelerometer used to monitor a sleep position of the infant as illustrated by block 114. The $CO_2$ sensor 104 may be used to monitor a $CO_2$ level around the nose and/or mouth of the infant as illustrated by block 116. The body temperature sensor 106 may, in some embodiments, be a thermistor used to monitor a body temperature of the infant as illustrated by block 118. The ambient temperature sensor 108 may also, in some embodiments, be a thermistor. The ambient temperature sensor 108 may be used to monitor an ambient temperature of the infant's environment as further illustrated by block 118. The respiration sensor 110 may, in some embodiments, be a microphone that can monitor the breathing sounds of the infant as illustrated by block 120. Similarly, ambient noise sensor 112 may also be a microphone, this microphone, however, is used to monitor ambient noise as further illustrated by block 120. The ambient noise may be subtracted from the breathing sounds to derive acoustic signals corresponding to the true breathing sounds of the infant.

Each of these monitoring parameters may then be used to determine whether the infant is being exposed to an environmental risk factor which may progress to SIDS. One such environmental risk factor may be a prone sleep position or a side (lateral) sleep position as illustrated by block 122. Such a risk factor is determined from the information or data obtained by the sleep position sensor 102. Other environmental risk factors can be determined from the $CO_2$ sensor 104. These risk factors may include $CO_2$ accumulation around the infant and/or $CO_2$ rebreathing by the infant as illustrated by block 124. Finally, the information obtained from the body temperature sensor 106 and/or the ambient temperature sensor 108 may be used to determine whether the infant is overheating and/or feverish as illustrated by block 126.

These environmental risk factors may then be used to evaluate whether the infant is in a risky sleep state or event. Representatively, if it is determined that the infant is in a prone position or a side position (block 122), it may be concluded that the infant is sleeping in an unsafe position as illustrated by block 128. If, in combination with the unsafe sleep position (block 128), it is determined that $CO_2$ is accumulating near the infant and/or the infant is rebreathing $CO_2$ (block 124), it may be determined that the infant's face is wedged in bedding as illustrated by block 130. This in turn, suggests that the infant's airway may be compromised and/or apnea is occurring (block 134). An infant with a comprised airway and/or apnea is at risk for SIDS as illustrated by block 136. The infant should therefore be immediately checked and a position of the infant changed to a safer position.

Another risky sleep state or event suggested by $CO_2$ accumulation and/or $CO_2$ rebreathing (block 124) in combination with overheating and/or fever (block 126) is head or face covering by bedding as illustrated in block 132. A head or face covered by bedding in turn suggests that the infant's airway may be compromised and/or apnea is occurring (block 134). An infant with a comprised airway and/or apnea is at risk for SIDS as illustrated by block 136. The infant should therefore be immediately checked and a position of the infant changed to a safer position.

Each of the sensors and their integration within a monitoring device will now be described in more detail in reference to FIGS. 2A-4B.

Figure 2A:
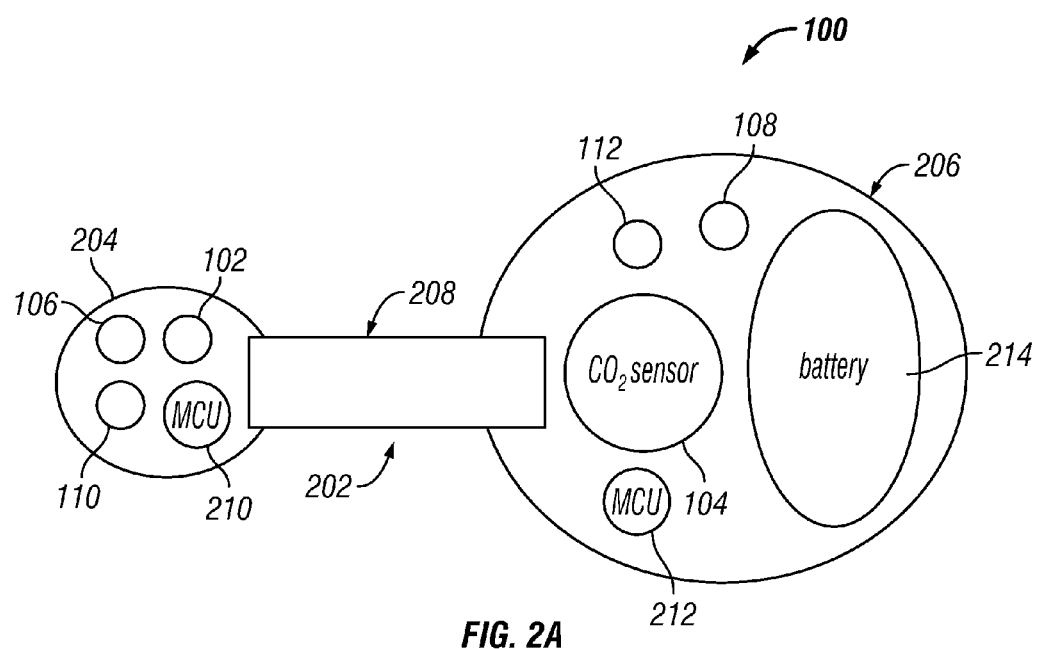
FIG. 2A illustrates a top plan view of an embodiment of an infant monitoring device.
Figure 2B:
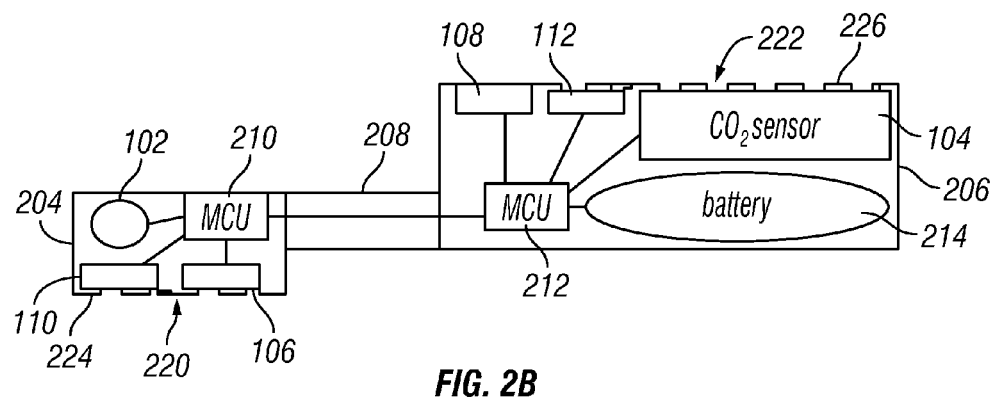
FIG. 2B illustrates a side cross-sectional view of the infant monitoring device of FIG. 2A.

FIG. 2A shows a top plan view of one embodiment of a monitoring device and FIG. 2B shows a cross-sectional side view of the device of FIG. 2A. Monitoring device 100 may be formed by a housing 202 that defines one or more compartments for containing the various components of device 100. Housing 202 may be dimensioned such that the one or more compartments may be positioned at a suprasternal notch or upper chest area of the infant. The suprasternal notch is chosen because it is: (1) the center of the torso, therefore, suitable for sleep position sensing; (2) directly over the trachea, to sense airway sounds; and (3) very close to the nose, for sensing $CO_2$ level in expired air. It has been found that when infants, 1-6 months of age, sleep face down that causes $CO_2$ levels around the nose to rise to 3%, the $CO_2$ level at the neck and upper chest can be detected at 1-2%.

In one embodiment, housing 202 may include a first compartment 204 and a second compartment 206. First compartment 204 may be dimensioned such that it can be attached to a portion of the infant's skin at the suprasternal notch. In this aspect, first compartment 204 can be dimensioned to contain components of device 100 that should be positioned closest to the infant's face during monitoring. For example, first compartment 204 may be dimensioned to contain sleep position sensor 102, respiration sensor 110 and temperature sensor 106. First compartment 204 may also contain a microcontroller (MCU) 210. Second compartment 206 may be dimensioned to contain the remaining components including components necessary for operation of device 100. For example, second compartment 206 can contain $CO_2$ sensor 104, ambient noise sensor 112, ambient temperature sensor 108, battery 214, and MCU 212. In this aspect, second compartment 206 may be larger than first compartment 204. The compartments may, however, be the same size or first compartment 204 may be larger than second compartment 206 depending upon the components that are to be contained therein. The bridge between first and second compartments can be made of rigid or flexible materials. The bridge will be used for electrical connections to supply power to first compartment 204 from the battery in the second compartment 206, and to transfer sensor signals between the two compartments. In one embodiment, first compartment 204 and second compartment 206 are in a non-planar arrangement. During operation, first compartment 204 can be attached to the skin at the suprasternal notch using, for example, a layer of hypoallergenic adhesive hydrogel. When the first compartment sensors have inadequate skin contact, such as device misplacement or movement artifacts, an indicator light will flash to alert the parents. Second compartment 206 can be placed on the top of the subject's clothing and secured to the clothing by, for example, buttons, straps or a hook and loop fastener such as Velcro®, or can be placed in a pocket or pouch that is secured to the infant's clothing.

In the illustrated embodiment, first compartment 204 and second compartment 206 are separate compartments attached to one another by, for example, connecting arm 208. Connecting arm 208 provides sufficient space between the two compartments such that first compartment 204 can be positioned at the suprasternal notch while second compartment 206 is positioned over the subject's clothing. In addition, connecting arm 208 can provide a conduit for electrical connections and wiring between components within first compartment 204 and second compartment 206. Although two separate compartments are illustrated, it is further contemplated that more than two compartments may be included and the compartments may be open to one another or housing 202 may form a single compartment, which contains each of the above-discussed components. Still further, first compartment 204 and second compartment 206 may be dimensioned to contain more or less of the previously discussed components. An overall size of housing 202, including first compartment 204 and second compartment 206, may be relatively small, for example, from about 60 mm to about 70 mm long and from about 30 mm to about 40 mm wide, but large enough so as not to be a choking hazard for the infant.

Housing 202 may be a substantially rigid structure that is made, for example, from a plastic or plastic-like material. Alternatively, housing 202 may be a compliant structure such that it can bend to conform to the dimensions of the surface upon which it is attached. For example, housing 202 may be made of a fabric or polymer material suitable for containing the sensors, such as, for example, a neoprene material.

Each of the internal components of device 100 will now be described in more detail. In one embodiment, sleep position sensor 102 may be any type of sensor capable of monitoring and/or detecting movement of the subject. Representatively, sleep position sensor 102 may be a triaxial accelerometer based on the digital output type piezo-resistive 3-axis acceleration sensor (HAAM-372). Such accelerometers have the range of ±2 g and ±8 g, and the digital output minimizes noise. The accelerometer is electronically connected to MCU 210 and passes signals thereto. The accelerometer may include a programmable threshold detection function, such that MCU 210 can be put to sleep and awakened by motion triggering. Any algorithm, which may be implemented within MCU 210 or the main processing unit, for sleep position identification based on an accelerometer output can be used to determine the sleep position of the subject.

Respiration sensor 110 may be any type of sensor capable of monitoring an air flow or respiration of the subject. Representatively, respiration sensor 110 may be an acoustic sensor having on-board analog signal filtering which detects a respiratory sound created when the subject inhales and exhales. For example, respiration sensor 110 may be an electret or piezoelectric acoustic sensor such as a microphone. In still further embodiments, a suitable acoustic sensor may include a relatively thin MEMS type sensor. Respiration sensor 110 is electronically connected to MCU 210 and passes signals thereto. In some embodiments, signals from the sensor may be amplified, then passed through a low pass filter before being recorded and digitized by MCU 210. Audio signals can be sampled at approximately 22 Hz, slow enough to reduce power and bandwidth requirements of device 100, while fast enough to preserve the respiratory signature. The audio signals will be processed in a local gateway associated with device 100, which can perform high speed analysis and extract the signature of respiratory cycles for further evaluation.

Temperature sensor 106 may be any type of sensor capable of monitoring a temperature of the infant. In one embodiment, temperature sensor 106 is a thermistor, such as the 402 medical probe sensor from Measurement Specialties (Hampton, Va.). Typical sensitivities for these thermistors are 0.1° C. Temperature sensor 106 should be placed in device housing 202, separate from the main electronics to reduce thermal coupling to the circuitry of MCU 210. Temperature sensor 106 is electronically connected to MCU 210 and passes signals thereto. Temperature sensor 106 can be interrogated once per second, and then the collected data can be stored in MCU 210 for reporting to, for example, the wireless gateway.

Temperature sensor 108 may be any type of sensor capable of monitoring a temperature of the ambient environment. Similar to temperature sensor 106, temperature sensor 108 may be a thermistor. Temperature sensor 108 may be electronically connected to MCU 212 and passes signals thereto. As can be seen from FIG. 2B, temperature sensor 106 may be positioned within a portion of first compartment 204 which faces the infant's skin while temperature sensor 108 is positioned along a portion of second compartment 204 which faces the environment. These portions of compartments 204 and 206 may include openings 220 and 222, respectively, which allow the sensors to monitor the temperature of the subject or the environment directly. Openings 220, 222 may be covered by a protective material 224, 226, respectively, that protects the device while still allowing for heat transfer to the sensors (e.g. a metal). Respiration sensor 110 may also be positioned near opening 220 of first compartment 204 such that it is near the infant's body an can detect breathing sounds through opening 220.

$CO_2$ sensor 104 may be any type of sensor capable of monitoring a $CO_2$ level of the subject. $CO_2$ sensor 104 is electronically connected to MCU 212 and passes signals thereto. In one embodiment, $CO_2$ sensor 104 is an optical sensor. Representatively, $CO_2$ sensor 104 may be an optical sensor that utilizes indicator dyes co-incorporated into a nanoporous matrix to measure $CO_2$ optically. For example, $CO_2$ sensor may be an optical sensor such as the EE892 Series optical sensor for OEM.

$CO_2$ sensor 104 may be designed such that it is capable of measuring $CO_2$ levels between 0.25% and 4% with fast response (in seconds) and sufficient sensitivity to detect $CO_2$ concentration levels considered to be a SIDS risk factor. Representatively, $CO_2$ sensor 104 may detect $CO_2$ concentrations in a range of from 0 to 100 mmHg with ±1 mmHg accuracy and 10 second response time. $CO_2$ sensor 104 may be relatively small in that it has an overall volume of 1 $cm^3$ or less.

Although an optical $CO_2$ sensor 104 is illustrated and described, it is further contemplated that an electrochemical $CO_2$ sensor may be used as an alternative.

Ambient noise sensor 112 may be any type of sensor capable of monitoring sounds from the ambient environment. Representatively, ambient noise sensor 112 may be an electret or piezoelectric acoustic sensor such as a microphone. In still further embodiments, a suitable acoustic sensor may include a relatively thin MEMS type sensor. Ambient noise sensor 112 is electronically connected to MCU 212 and passes signals thereto. In some embodiments, signals from the sensor 112 may be subtracted from signals from the respiration sensor 110 to determine a signal indicative of a breathing pattern of the infant, without any ambient noise interference.

$CO_2$ sensor 104 and ambient noise sensor 112 may be positioned near opening 222 of second compartment 206 so that they can monitor the desired environmental factors. The portion of opening 222 over $CO_2$ sensor 104 and ambient noise sensor 112 may be covered by an acoustically transparent material that allows for air flow from the ambient environment to the sensors while still providing a protective barrier against contaminants (e.g. dust).

Device 100 may also include a battery 214 to provide power to each of the sensors and MCU 210, 212 within device 100. Battery 214 may be, in some embodiments, a lithium polymer battery, which can be custom ordered from manufacturers. Lithium polymer batteries have high charge densities and good power densities, which are needed for burst (peak-power) processing patterns. Such a battery can be as lightweight as 1.2 grams with a capacity of 90 mAh at 3.7-4.2 V. Battery strength can be monitored periodically by MCU 210 or MCU 212.

Figure 3A:
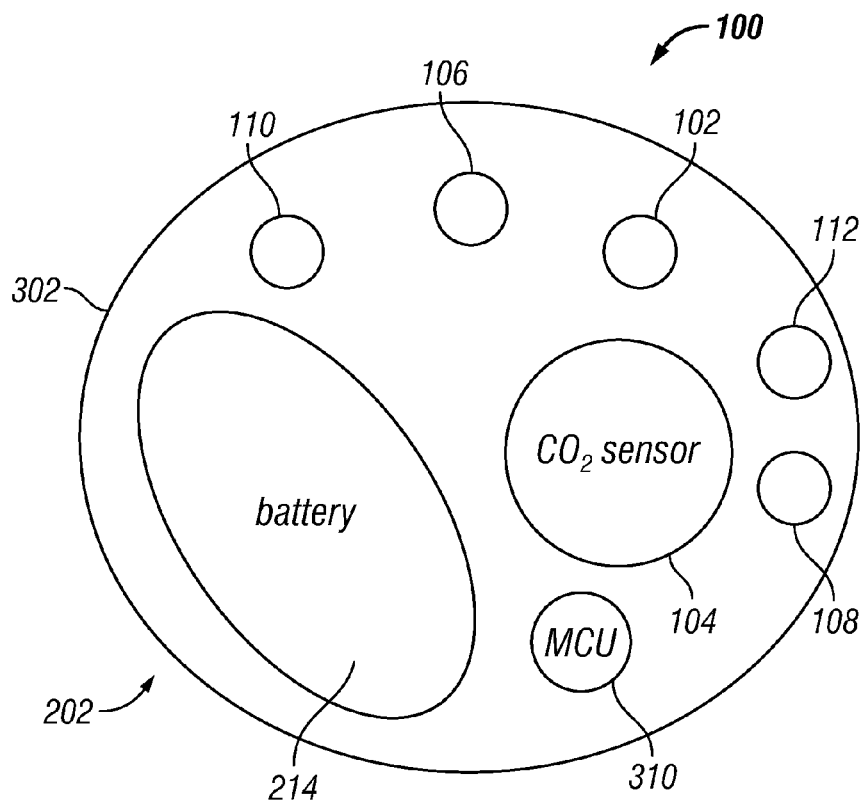
FIG. 3A illustrates a top plan view of another embodiment of an infant monitoring device.
Figure 3B:
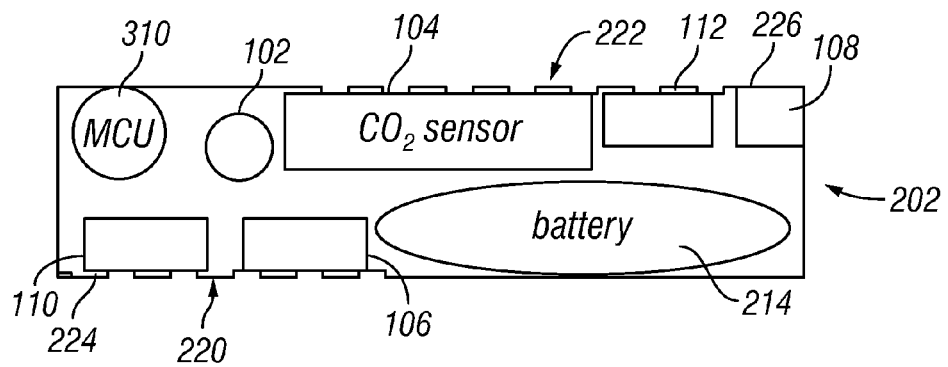
FIG. 3B illustrates a side cross-sectional view of the infant monitoring device of FIG. 3A.

FIG. 3A shows a top plan view of another embodiment of a monitoring device and FIG. 3B shows a cross-sectional side view of the device of FIG. 3A. In this embodiment, device 100 includes all of the same components as described in reference to FIG. 2A and FIG. 2B, except that in this embodiment, housing 202 includes a single compartment 302. In this aspect, each of the sleep position sensor 102, respiration sensor 110, temperature sensor 106, $CO_2$ sensor 104, ambient noise sensor 112, ambient temperature sensor 108, and battery 214 are contained within the same compartment. Housing 302 may also contain a single MCU 310 as shown. It is contemplated, however, that more than one MCU may be used, but is not required. Opening 220 and opening 222 may be positioned on opposing sides of housing 202. Opening 220 and opening 222 may be covered by a protective material 224, 226, respectively, that provides a protective barrier against contaminants (e.g. dust). Such material may be, for example, a mesh or other similar material that protects against contaminants but still allows for air to pass through it. In some portions of openings 220, 222 the material may be a material that allows for heat transfer (e.g. a metal). For example, the portions of openings 220 and 222 over temperature sensors 106 and 108, may be covered by a metal material that protects the device while still allowing for heat transfer to the sensors (e.g. a metal). The portions of opening 222 over $CO_2$ sensor 104, respiration sensor 110 and ambient noise sensor 112 may be covered by an acoustically transparent material that allows the sensors to detect $CO_2$ levels and/or noises from the infant and environment.

Figure 4A:
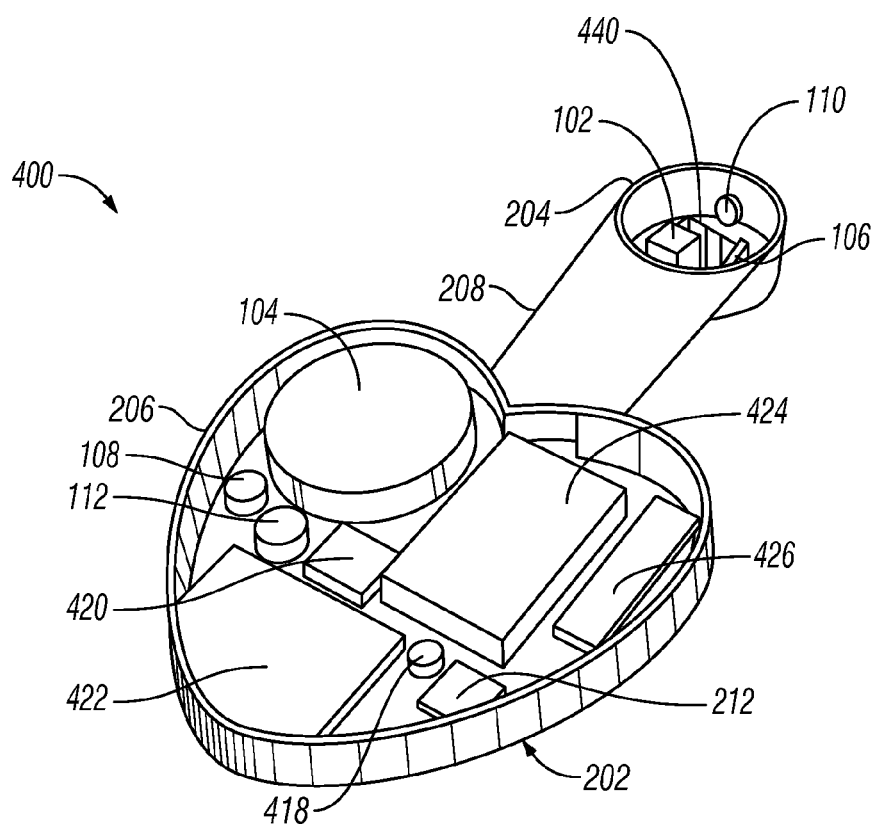
FIG. 4A illustrates a perspective view of an embodiment of an infant monitoring device.
Figure 4B:
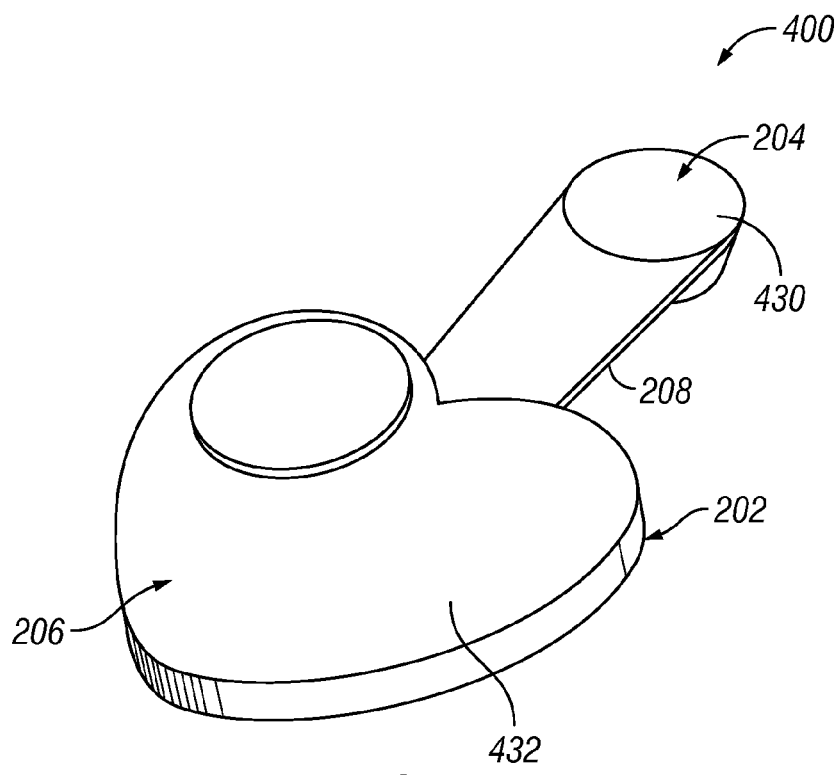
FIG. 4B illustrates a perspective view of an embodiment of the infant monitoring device of FIG. 4A having a cover.

FIG. 4A and FIG. 4B illustrate perspective views of another embodiment of a monitoring device. FIG. 4A illustrates monitoring device 400 with cover members 430 and 432 removed so that the internal components can be seen more clearly.

Monitoring device 400 may be formed by a housing 202 that defines one or more compartments for containing the various components of device 400. Housing 202 may be dimensioned such that the one or more compartments may be positioned at a suprasternal notch of the subject. In one embodiment, housing 402 may include a first compartment 404 and a second compartment 406. First compartment 404 may be dimensioned such that it can be attached to a portion of the subject's skin at the suprasternal notch. In this aspect, first compartment 404 can be dimensioned to contain components of device 400 that should be positioned closest to the infant's face during monitoring. For example, first compartment 404 may be dimensioned to contain sleep position sensor 102, respiration sensor 110 and temperature sensor 106, which are identical to those previously discussed in reference to the previous figures. Although not illustrated, an MCU may further be contained within compartment 404.

Second compartment 406 may be dimensioned to contain the remaining components including components necessary for operation of device 400. For example, second compartment 406 can contain $CO_2$ sensor 104, temperature sensor 108 and ambient noise sensor 108, which are identical to those previously discussed in reference to the previous figures. Second compartment may also contain inductor 418, voltage regulator 420, memory card 422, battery 424, antenna 426 and MCU 428. In this aspect, second compartment 406 may be larger than first compartment 404. The compartments may, however, be the same size or first compartment 404 may be larger than second compartment 406 depending upon the components that are to be contained therein. In one embodiment, first compartment 404 and second compartment 406 are in a non-planar arrangement. During operation, first compartment 404 can be attached to the skin at the suprasternal notch using, for example, a layer of hypoallergenic adhesive hydrogel. Second compartment 406 can be placed on the top of the subject's clothing and secured to the clothing by, for example, buttons, straps or a hook and loop fastener such as Velcro®.

In the illustrated embodiment, first compartment 404 and second compartment 406 are separate compartments attached to one another by, for example, connecting arm 408. Connecting arm 408 provides sufficient space between the two compartments such that first compartment 404 can be positioned at the suprasternal notch while second compartment 406 is positioned over the subject's clothing. Connecting arm 408 8 is further dimensioned to provide a conduit for wires or other components extending between components within the first and second compartments 404, 406. An overall size of housing 402, including first compartment 404 and second compartment 406, may be relatively small, for example, from about 60 mm to about 70 mm long and from about 30 mm to about 40 mm wide.

Housing 402 may be a substantially rigid structure that is made, for example, from a plastic or plastic-like material. Alternatively, housing 402 may be a compliant structure such that it can bend to conform to the dimensions of the surface upon which it is attached. For example, housing 402 may be made of a fabric or polymer material suitable for containing the sensors, such as, for example, a neoprene material.

As illustrated in FIG. 4B, housing 402 may further include cover member 430 and cover member 432 that can be placed over first compartment 404 and second compartment 406, respectively, to enclose and protect the components contained therein. In some embodiments, cover members 430, 432 form a water resistant-enclosure. In this aspect, module housing 402 can be cleaned and/or sanitized between uses. One or both of cover members 430, 432 may also be removable so that the internal components may be removed and/or replaced as necessary.

In some embodiments, it is contemplated that device 400 may be inductively charged using inductor 418, which may be an inductive coil. In this aspect, monitoring device 400 can include metallic pads, for example gold plated pads, formed on the outer surface of housing 402, to facilitate recharging (by magnetic connection to a recharging plate) and possibly reprogramming of the device. Voltage regulator 420 may further be provided to control and/or regulate an electric current used to operate one or more of sensors 110, 112, 114 and 116.

MCU 212 may be any standard MCU, which includes, for example, a processor core, memory, and programmable input/output peripherals. In addition to monitoring the various operations of device 400 (e.g., the battery strength), MCU 212 can be used to process information obtained by one or more of sensors 102, 104, 106, 108, 110, and 112 and output such information to, for example, the main processing unit (e.g. a computer). MCU 212 may further include a radio. The radio may be a low power radio with a range of approximately 10 to 50 meters at 1 mW of RF power. The radio in conjunction with antenna 426 may be used to transmit signals to and from device 400 as described in reference to FIG. 5.

In addition to a memory component integrated within MCU 212, memory card 422 may be included in device 400. Memory card 422 may be any type of electronic flash memory data storage device used for storing digital information, e.g., information from sensors 102, 104, 106, 108, 110, and 112.

One or more of sensors 102, 104, 106, 108, 110, and 112 may be installed on a wireless transmission platform 440. The wireless transmission platform 440 can be used for wireless transmission of data obtained by sensors 102, 104, 106, 108, 110, and 112 to a remote location. Representatively, as illustrated in FIG. 4A, sleep position sensor 102 and temperature sensor 106 can be installed on wireless transmission platform 440.

Figure 5:
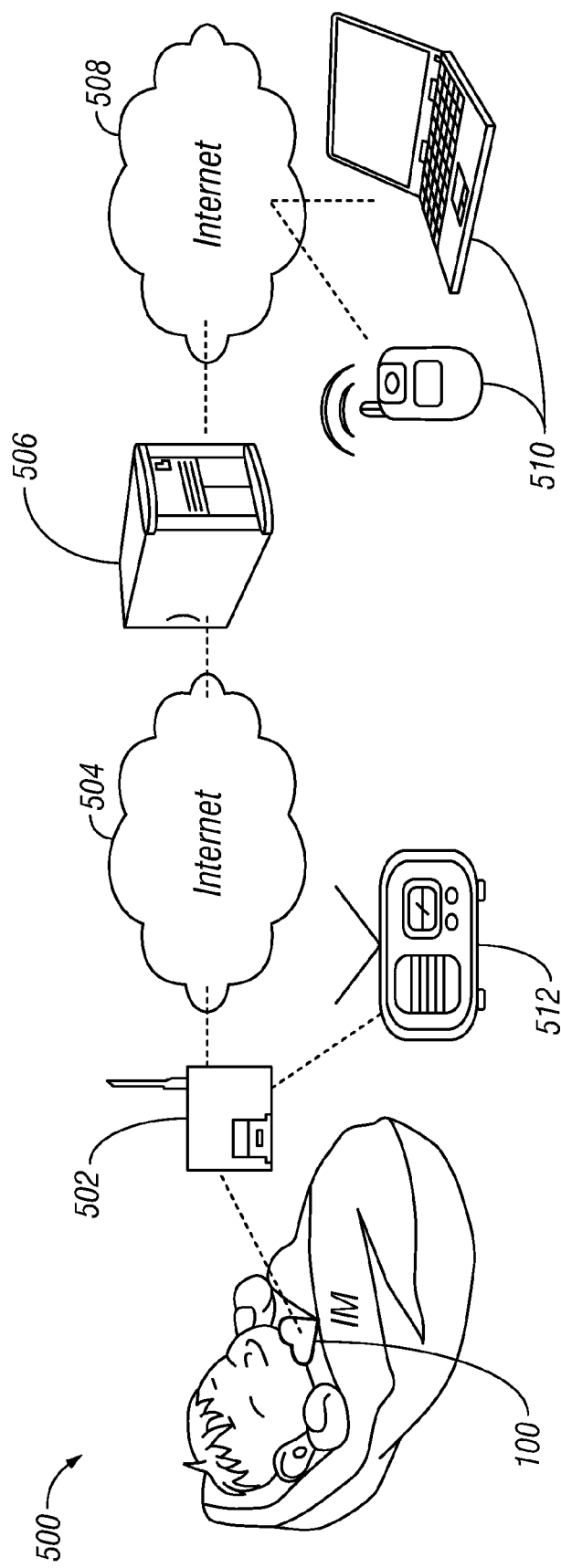
FIG. 5 illustrates a schematic diagram of one embodiment of an infant sleep environment monitoring system for local and remote monitoring.

FIG. 5 illustrates a schematic drawing of one embodiment of a SIDS monitoring system. In this embodiment, it can be seen that system 500 includes a wireless network platform for onsite and remote monitoring. The wireless network may include gateway 502 by the crib, an optional relay unit to extend the wireless range in the home, and a remote monitoring server (RMS) 506. The local gateway 502 communicates wirelessly with one or more of device 100 and sends data to the RMS through standard Internet connections 504. Some preprocessing is performed on the local gateway 502, and critical alarms are sent directly to a local monitor 512 without the need to pass through the Internet 504. The RMS 506 can be a computer in a secure network that archives data from multiple sources and provides the data for analysis or monitoring by remote monitors 510, which may include a desktop computer, a portable computer or a web-enabled smart phone. The RMS 506 can also provide data updates to non-web cell phones as SMS or voice messages. The gateway is responsible for receiving data from device 100 and providing a route to the server on the Internet 504. The gateway 502 consists of a microcontroller with a built-in Ethernet controller, a USB or Secure Digital (SD) card slot, and wireless transceivers to communicate with the infant monitoring device. The gateway system may be configured from a PC or may be a custom-made gateway based on an ARM-9 network processor from ASIX84 or on the Freescale Coldfire M52259. Alternatively, custom boards may be constructed so that when resetting is needed, the system can boot up in a fraction of a second, as compared to a minute on a PC.

Gateway 502 can contain the local intelligence for generating alerts to caregivers. An algorithm (see Table 1) will be installed in the gateway to detect "risky sleep states" (RSS's) of the infants. In the event of an RSS, the gateway issues alerts to the local monitor 512 (a computer or other network connected devices) to make audio/visual alarms on site, or to the RMS 506.

It is noted that although a local gateway 502 is illustrated, in some embodiments, the wireless transmission platform may be a Bluetooth technology implemented within monitoring device 100 and local gateway may be omitted 502. The Bluetooth technology may allow for wireless transmission of data from monitoring device 100 to a smartphone or other handheld device capable of displaying the data locally or remotely.

Device 100 may be configured to use a low power radio to conserve battery life and for safety considerations. The range will be approximately 10 to 50 meters at 1 mW of RF power. If the range of device 100 is not sufficient, relay nodes may be provided to extend the effective range of device 100. One possibility will be to place a relay node on the crib or in the bedroom to relay the data to the main gateway.

RMS 506 may be a database system that is hosted by a computer server. The purpose of RMS 506 is to receive data from the gateway over the Internet and log the data into databases for individual infants. In the case of a critical RSS—such as high $CO_2$ or apnea, the RMS will generate alerts, such as instant messaging, text messages, phone calls with a synthesized message, or other pre-determined forms of notification, in addition to alarms by the gateway. Thus, the gateway 502 produces local alerts, whereas the RMS 506 both receives alerts from the gateway (and logs the events) and generates its own alerts. The RMS 506 can also provide a web interface to its users and service providers. This will give users with web browsers (including those on smart phones) instant access to current status from anywhere. Applications (apps) for smartphone users will be available for common operating systems (such as iOS, Android and Windows) to gain direct access to RMS 506 and follow the monitoring of an infant in real time.

An algorithm for sleep state assessment and risky sleep state (RSS) classification can be installed in the gateway. In the algorithm, the cutoff points of the sensor data and risk levels are based on current experimental studies, and these values can be adjusted as more information becomes available. Accelerometers detect body position by angle of rotation as a continuous variable. However, output data will indicate one of the 3 sleep positions—supine (face up, rotation)<45°, side (rotation 45° to 134°), and prone (face down, rotation 135° to 180°). The continuous variable of $CO_2$ level will be categorized as <1%, 1-3.9%, and ≥4%. It has been found that head covering can raise body temperature by 0.4° C. Therefore, a rise in temperature of ≥0.5° C. above baseline will be considered significant.

An "event" is defined as one of the following changes in the infant's sleep: (1) turning from supine to the side or prone position; (2) wedging of the face within bedding; or (3) a blanket covering the head. An RSS is a considered a "state" of sleep, generally following an event, with clinically significant changes in $CO_2$, temperature, or respiration. An event may or may not lead to an RSS. Some events are cleared by infants (e.g. the infant turns back to the supine position) without turning into an RSS.

SIDS risk factors may occur alone or follow a sequence, and the interactions among risk factors can be complex. For example, an infant rolls to the prone position, followed minutes later by a rise in $CO_2$. Or, after a blanket covers an infant's head, the $CO_2$ level rises, and the temperature also rises due to poor heat dissipation. From the sequence of outputs of the sensors in device 100, likely scenarios of the events and risky states are constructed, and the risk levels associated with the scenarios classified. In the algorithm, the sequences of events are identified, the sleep state is deduced, and the associated risk level for SIDS occurrence is determined. The current classifications for the RSS risk levels are Low, Increased, Moderate, High, and Emergency as shown in Table 1 below. This classification system as well as the values used in the system can be further adjusted as more research data become available.

TABLE 1

Five levels of RSS with probable scenarios in the infant's sleep environment.

| Risk Level | Measures | | | | |
| --- | --- | --- | --- | --- | --- |
| | Sleep Position | Body Temperature | $CO_2$ Level | Airway Flow | Probable Scenarios |
| Low Risk | Supine | Normal | <1% | Normal | Normal sleep |
| Increased Risk | Supine | Rise ≥0.5° C. | <1% | Normal | Head covering or overheating |
| | Side or Prone | Normal | <1% | Normal | Side or prone sleep, otherwise normal |
| Moderate Risk | Supine | Normal | 1% to 3.9% | Normal | Head covering & $CO_2$ rebreathing |
| | Supine | Rise ≥0.5° C. | 1% to 3.9% | Normal | Head covering & overheating |

TABLE 1-continued

Five levels of RSS with probable scenarios in the infant's sleep environment.

| Risk Level | Sleep Position | Body Temperature | CO$_2$ Level | Airway Flow | Probable Scenarios |
|---|---|---|---|---|---|
| | Side or Prone | Normal | 1% to 3.9% | Normal | Face wedging & CO$_2$ rebreathing |
| | Side or Prone | Rise ≥0.5° C. | 1% to 3.9% | Normal | Face wedging & head covering |
| High Risk | — | — | ≥4% | Normal | CO$_2$ rebreathing risk for apnea |
| Emergency | — | — | — | NO flow | Apnea |

The above identified algorithm for RSS identification and classification can be installed in the gateway, so that onsite alerts can be generated in the event of a significant RSS. Sequences of events can be simulated in the physiology lab, to confirm that the sensors accurately detect the changes, and that the algorithm correctly follows the sequence of changes that are used to determine the risk levels.

An algorithm specifically designed for general and/or individualized infant sleep risk assessment (ISRA) at home may further be installed in the gateway. In particular, with respect to an individualized algorithm, infants have different responses to events during sleep, and the risks associated with an RSS may also differ among infants. For example, with the head covered, some infants keep the CO$_2$ level under 1%, whereas other infants have CO$_2$ levels over 4%. Prone sleep position carries a much higher risk for infants who do not have prone sleeping experience, compared to infants who have such experience. Therefore, a Moderate Risk state as classified by the general RSS algorithm, may pose a moderate risk for one infant but a low risk for another. The ISRA algorithm is therefore intelligent, taking into account each infant's individual sleep patterns, so as to optimize risk classification. Infants who are candidates for in home use can be monitored for a period of time and then the ISRA algorithm refined based on the monitoring for individualized risk assessment.

The ISRA algorithm can be based on a model independent analysis and capable of mapping the likelihood of SIDS over a space of several indicating variables. Alternatively, it can be based on a rational common sense approach to analysis that is best described as "deviation from normal" analysis. In this analysis an assumption is made that the farther an infant deviates from normal sleeping patterns, the more likely the infant is at risk (i.e., the higher the risk) for SIDS.

The ISRA algorithm is based on eight variables: sleep position, CO$_2$ level, temperature, and respiration, and the time derivatives of these 4 variables (i.e., how quickly they change). These 8 variables are used to form an 8-dimensional volumetric space that characterizes the infant's sleep state.

Representatively, a normalcy map such as a Gaussian spheroid ("normal" distribution) in accordance with the ISRA algorithm may be used to evaluate infant risks. The normalcy map may include a "normal" region of space which is the region having a relatively high probability that the infant will be in this portion of the space at any time. This is based on previously collected data for the particular infant. The normal region is therefore considered normal for the particular infant and does not pose a risk.

A probability distribution function is determined for the infant based on the historical data. When the infant enters a sleep state that is in a low probability section of the map, e.g., a "far from normal" region, then this is considered a "deviation from normal," and an alarm is set to warn the caregiver. Data analysis will be used to determine the shape of the "normal" region of space, which is the region with the most data. The regions outside of the normal region are considered risky, with those regions farthest from the normal region being the most risky and regions closer being the least risky.

Although a Gaussian spheroid ("normal" distribution) is described, it is contemplated that any type of distribution may be used that is found sufficient to identify trends based on collected dat. Once the probability function has been determined, a maximum likelihood fitting procedure is used to match the most likely function shape to the data. This allows for a probability map over the "space" of the infant's sleep, to identify conditions that significantly deviate from normal.

It is contemplated that once the initial data specific to an infant has been collected, the fitting and mapping procedures will be automated for that infant. This will allow individualized maps to be prepared so that alarms for risky states will be specific to the sleep patterns of each individual infant. Representatively, in one embodiment, the individualized algorithm for sleep risk assessment may be based on a magnitude of deviation from a normal sleep pattern of the infant from ranges and distribution measurements obtained during a previous monitoring operation. The normal sleep pattern ranges and distribution measurements for the individualized algorithm may take into account parameters such as sleep position, body temperature, carbon dioxide levels, respiration sounds and time derivatives (rate of changes) of the parameters.

Figure 6:
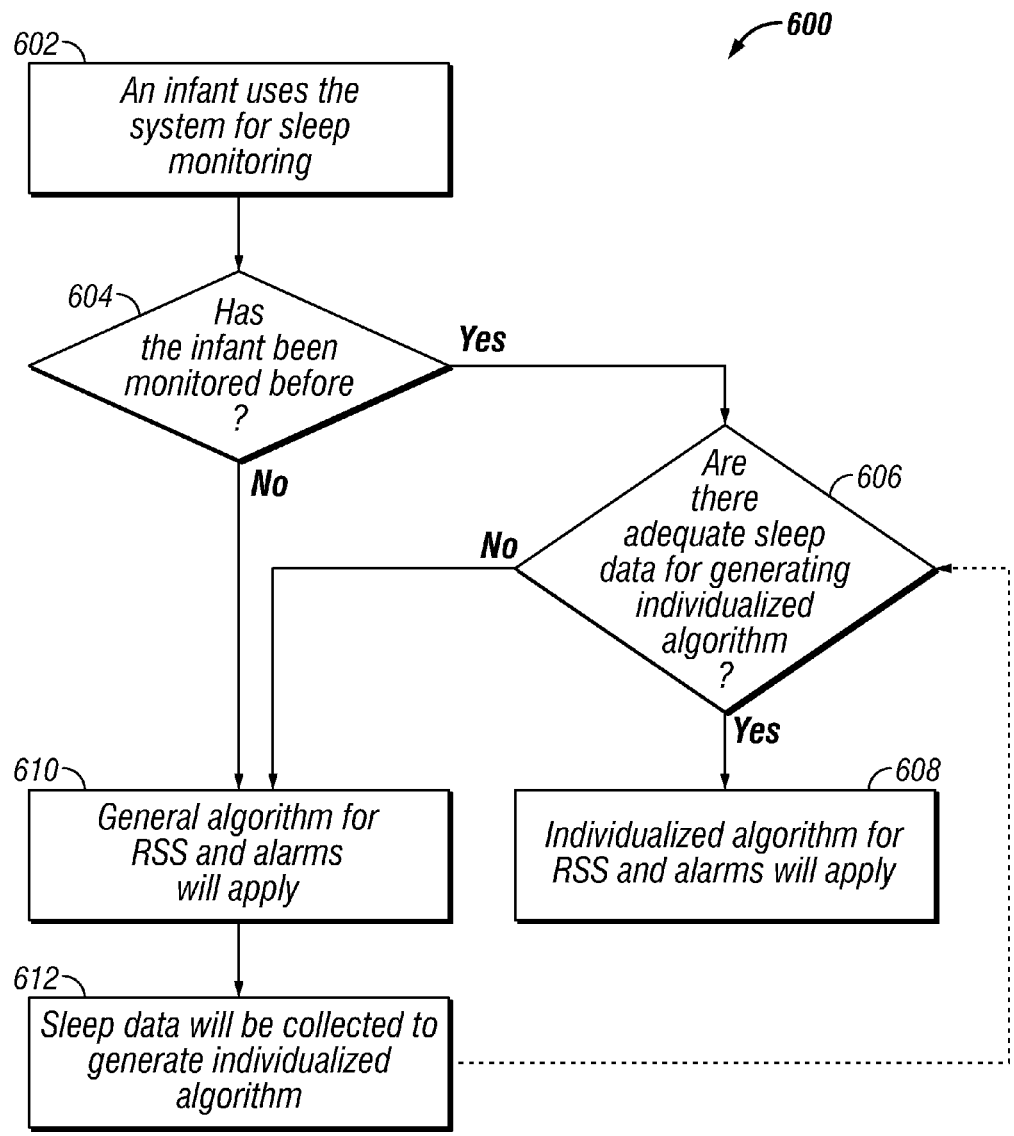
FIG. 6 illustrates one embodiment of an algorithm for determining whether to monitor an infant for the presence of SIDS risk factors using a general or individualized algorithm.

FIG. 6 illustrates a flow chart of one embodiment of an algorithm for determining whether to use a general or individualized (intelligent) sleep risk assessment algorithm with a particular infant. The determining algorithm 600 includes determining whether the infant is to use the SIDS monitoring device for sleep monitoring (block 602). If the device (e.g. monitoring device 100 or 400) is to be used, the next step is to determine whether the infant has been monitored before (block 604). If the answer is yes, the system evaluates whether adequate sleep data is available from that infant for generating the individualized algorithm (block 606). If there is sufficient data, it is determined that the individualized algorithm for RSS and alarms should be used with that particular infant (block 608). If, on the other hand, the infant has not been monitored before or there is insufficient data to generate an individualized algorithm for that infant, the general algorithm for RSS and alarms should be used (block 610). Sleep data can then be collected for the infant so that an individualized algorithm can be constructed (block 612).

Figure 7:
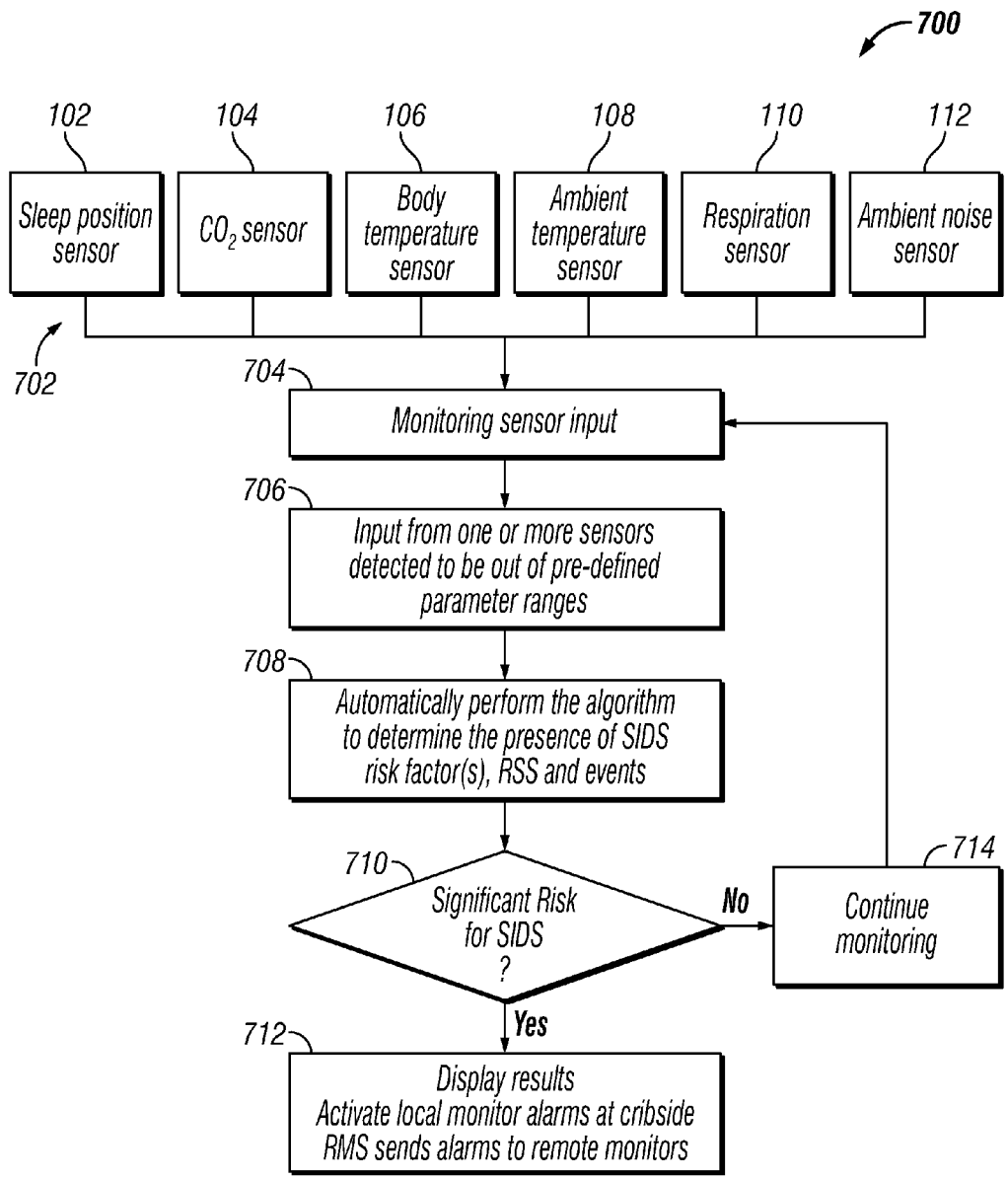
FIG. 7 illustrates one embodiment of a general algorithm for monitoring and determining presence of SIDS risk factors, and assigning the level of risk in order to generate local and remote alarms.

FIG. 7 illustrates a flow chart of one embodiment of a system for monitoring an infant for SIDS risk factors according to the general algorithm. System 700 may include sensors 702. Sensors 702 may be any one or more of the previously discussed sensors 102, 104, 106, 108, 110 and/or 112. System 700 may monitor an input from any one or more of the sensors (block 704). The input may be monitored to detect any input data outside of a pre-defined non-risky parameter range (block 706). If data outside of the pre-defined parameter range is detected, the system automatically performs the general algorithm to determine the presence of SIDS risk factors, RSS and events (block 708). If a significant risk for SIDS is detected (block 710), the results are displayed and an alarm is activated, for example, at the local monitor alarm at the crib side. The remote monitoring server (RMS) can then send the alarm to the remote monitor (block 712). If, on the other hand, it is determined that there is not a significant risk for SIDS, the system continues monitoring sensor input (block 714).

Figure 8:
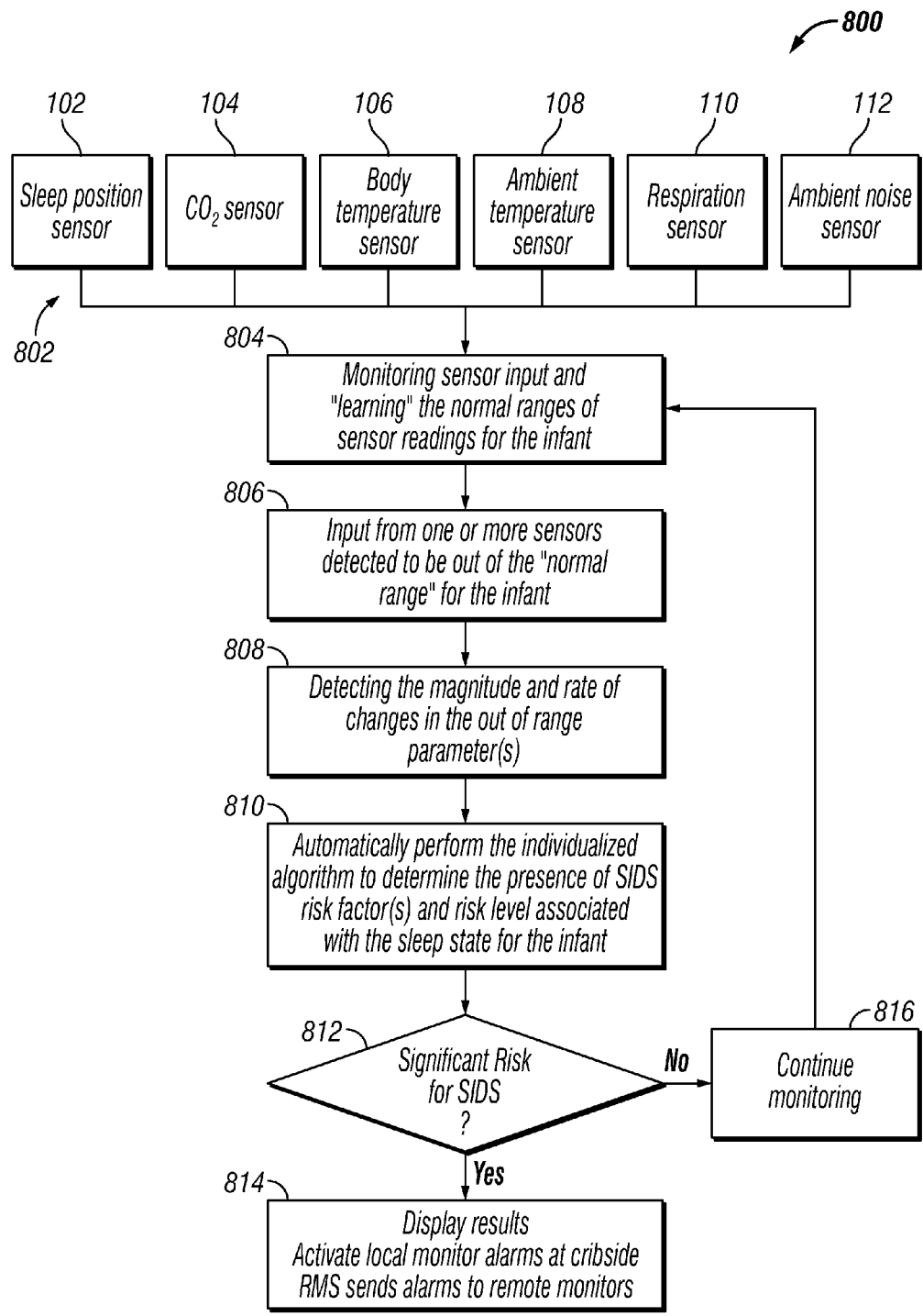
FIG. 8 illustrates one embodiment of an individualized "intelligent" algorithm for monitoring and determining presence of SIDS risk factors, and assigning the level of risk in order to generate local and remote alarms.

FIG. 8 illustrates a flow chart of one embodiment of a system for monitoring an infant for SIDS risk factors according to an individualized algorithm. System 800 may include sensors 802. Sensors 802 may be any one or more of the previously discussed sensors 102, 104, 106, 108, 110 and/or 112. System 800 may monitor an input from any one or more of the sensors and "learn" the normal ranges of sensor readings for the infant (block 804). The input may be monitored to detect any input data outside of a "normal range" for the infant (block 806). For example, information from any of the previously discussed sensors may be characterized as a first set of data corresponding to a first sleep pattern of the infant and a second set of data corresponding to a second sleep pattern of the infant. The individualized algorithm is then capable of comparing the first set of data to the second set of data to determine a difference between the first sleep pattern and the second sleep pattern to determine if the infant is at risk for SIDS. The magnitude and rate of changes in the out of range parameters are evaluated (block 808). The system then automatically performs the individualized algorithm to determine the presence of SIDS risk factor(s) and risk level associated with the sleep state of the infant (block 810). If a significant risk for SIDS is detected (block 812), the results are displayed and an alarm or other suitable alert is activated, for example, the local monitor alarm at the crib side. The remote monitoring server (RMS) can then send the alarm to the remote monitor (block 814). If, on the other hand, it is determined that there is not a significant risk for SIDS, the system continues monitoring sensor input (block 816).

Although specific algorithms are described in reference to FIG. 7 and FIG. 8, it is contemplated that based on the monitoring, the system may automatically perform any of the above-discussed algorithms to determine the presence of a SIDS risk factor. In one embodiment, the results may be displayed by the system. For example, the results may be displayed in an LCD display screen of an associated main processing unit such as a computer. In one embodiment, the algorithm performed by the system may include determining a sequence of events indicating a change in the subject's sleep state and determining a risk level for SIDS occurrence based on the subject's sleep state. Determining the risk level for SIDS occurrence may include classifying a detected SIDS risk factor, or a combination of SIDS risk factors, as a low risk, an increased risk, a moderate risk, a high risk or an emergency. The care provider may be automatically alerted by the system when the SIDS risk factor is classified as an emergency.

A device, such as RMS 506 or other main processing unit, for performing the operations herein may be specially constructed for the required purposes or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs and magnetic-optical disks, read-only memories (ROMs), random access memories (RAMs), EPROMs, EEPROMs, magnetic or optical cards, Flash memory devices including universal serial bus (USB) storage devices (e.g., USB key devices) or any type of media suitable for storing electronic instructions, each of which may be coupled to a computer system bus.

The algorithms and displays presented herein are not inherently related to any particular computer or other apparatus. Various general purpose systems may be used with programs in accordance with the teachings herein or it may prove convenient to construct a more specialized device to perform the described method. In addition, the invention is not described with reference to any particular programming language. It will be appreciated that a variety of programming languages may be used to implement the teachings of the invention as described herein.

A computer readable medium includes any mechanism for storing information in a form readable by a computer. For example, a computer readable medium includes read only memory ("ROM"), random access memory ("RAM"), magnetic disk storage media; optical storage media, flash memory devices or other type of machine-accessible storage media.

In the preceding detailed description, specific embodiments are described. It will, however, be evident that various modifications and changes may be made thereto without departing from the broader spirit and scope of the claims. The specification and drawings are, accordingly, to be regarded in an illustrative rather than restrictive sense.

What is claimed is:
1. A system comprising:
a monitoring device dimensioned for placement on an infant, the monitoring device having a plurality of sensors for monitoring a sleep position, a change in the sleep position, a temperature, a change in the temperature, a carbon dioxide level, a change in the carbon dioxide level, a respiration, and a change in the respiration of the infant; and
a processing unit coupled to the monitoring device, the processing unit capable of processing information from the plurality of sensors and performing an algorithm to identify a sequence of events, deduce a sleep state of the infant, and determine a risk level for sudden infant death syndrome (SIDS) based on the information,
wherein the risk level includes a low risk, an increased risk, a moderate risk, or a high risk,
wherein the low risk is identified when the infant has a supine sleep position, a normal body temperature, less than about 1% carbon dioxide levels, and normal respiration;
wherein the increased risk is identified when the infant has a) a supine sleep position, a rise of ≥0.5° C. in body temperature, less than about 1% carbon dioxide levels, and normal respiration or b) a supine sleep position or a prone sleep position, a normal body temperature, less than about 1% carbon dioxide levels, and normal respiration;
wherein the moderate risk is identified when the infant has a) a supine sleep position, a normal body temperature, between about 1% to about 3.9% carbon dioxide levels, and normal respiration, b) a supine sleep position, a rise of ≥0.5° C. in body temperature, between about 1% to about 3.9% carbon dioxide levels, and normal respiration, c) a supine sleep position or a prone sleep position, a normal body temperature, between about 1% to about 3.9% carbon dioxide levels, and normal respiration, or d) a supine sleep position or a prone sleep position, a rise of ≥0.5° C. in body temperature, between about 1% to about 3.9% carbon dioxide levels, and normal respiration; and wherein the high risk is identified when the infant has ≥4% carbon dioxide levels.

2. The system of claim 1 wherein the carbon dioxide level sensor optically detects the carbon dioxide level.

3. The system of claim 1 wherein the processing unit is a local monitoring unit, the system further comprising a remote monitoring unit.

4. The system of claim 1 further comprising:
a wireless network platform for onsite and remote monitoring.

5. The system of claim 1 wherein information from the plurality of sensors comprises a first set of data corresponding to a first sleep pattern of the infant and a second set of data corresponding to a second sleep pattern of the infant, and wherein an individualized algorithm is capable of comparing the first set of data to the second set of data to determine a difference between the first sleep pattern and the second sleep pattern.

6. The system of claim 1, wherein the processing unit is capable of processing the information about the sleep position, the change in the sleep position, the carbon dioxide level, the change in the carbon dioxide level, the temperature, the change in the temperature, the respiration, and the change in the respiration from the plurality of sensors to create an 8-dimensional volumetric space that characterizes the infant's sleep state and performing an individualized algorithm using a Gaussian spheroid on the 8-dimensional volumetric space to determine the SIDS risk level.

7. A method for monitoring a sleep environment that puts infants at risk for sudden infant death syndrome (SIDS), the method comprising:
monitoring using a monitoring device dimensioned for placement on an infant two or more of a sleep position, a change in the sleep position, a respiration, a change in the respiration, a temperature, a change in the temperature, a carbon dioxide level, and a change in the carbon dioxide level of the infant;
automatically performing an algorithm, based on the monitoring, to identify a sequence of events, deduce a sleep state of the infant, and determined a risk level for SIDS;
displaying a result of the algorithm; and
sending an alert based on the risk level,
wherein the algorithm classifies the SIDS risk level as one of a low risk, increased risk, moderate risk, high risk, or an emergency,
wherein the low risk is identified when the infant has a supine sleep position, a normal body temperature, less than about 1% carbon dioxide levels, and normal respiration;
wherein the increased risk is identified when the infant has a) a supine sleep position, a rise of ≥0.5° C. in body temperature, less than about 1% carbon dioxide levels, and normal respiration or b) a supine sleep position or a prone sleep position, a normal body temperature, less than about 1% carbon dioxide levels, and normal respiration;
wherein the moderate risk is identified when the infant has a) a supine sleep position, a normal body temperature, between about 1% to about 3.9% carbon dioxide levels, and normal respiration, b) a supine sleep position, a rise of ≥0.5° C. in body temperature, between about 1% to about 3.9% carbon dioxide levels, and normal respiration, c) a supine sleep position or a prone sleep position, a normal body temperature, between about 1% to about 3.9% carbon dioxide levels, and normal respiration, or d) a supine sleep position or a prone sleep position, a rise of ≥0.5° C. in body temperature, between about 1% to about 3.9% carbon dioxide levels, and normal respiration; and
wherein the high risk is identified when the infant has ≥4% carbon dioxide levels.

8. The method of claim 7 wherein the algorithm is an intelligent algorithm for individualized infant sleep risk assessment.

9. The method of claim 7 further comprising:
learning the infant's sleep pattern from repeated monitoring to generate an individualized algorithm for sleep risk assessment or determining if a general or an individualized algorithm should be used to determine the risk level of SIDS.

10. The method of claim 9 wherein the individualized algorithm determines a magnitude of deviation between a first normal sleep pattern of the infant determined by the monitoring and a second sleep pattern of the infant determined by the monitoring.

11. The method of claim 7 wherein a care provider is automatically alerted when the SIDS risk level is classified as an emergency, the care provider receives different alerts and recommended interventions for different risk levels for SIDS, or the care provider can adjust the alert to be sent to them for different levels of risk for SIDS.

12. The method of claim 7, wherein the processing unit is capable of processing the information about the sleep position, the change in the sleep position, the carbon dioxide level, the change in the carbon dioxide level, the temperature, the change in the temperature, the respiration, and the change in the respiration from the plurality of sensors to create an 8-dimensional volumetric space that characterizes the infant's sleep state and performing an individualized algorithm using a Gaussian spheroid on the 8-dimensional volumetric space to determine the SIDS risk level.

13. An apparatus comprising:
a housing dimensioned for placement along a suprasternal notch region of an infant, the housing having a first compartment and a second compartment;
a plurality of sensors for monitoring a sleep position, a change in the sleep position, a temperature, a change in the temperature, a respiration of the infant and a change in the respiration of the infant positioned within the first compartment;
a carbon dioxide sensor for monitoring a carbon dioxide level of the infant and a change in the carbon dioxide level of the infant positioned within the second compartment; and
a processing unit coupled to the plurality of sensors and the carbon dioxide sensor, the processing unit capable of processing information from the plurality of sensors and the carbon dioxide sensor and performing an algorithm to identify a sequence of events, deduce a sleep state of the infant, and determined a risk level for sudden infant death syndrome (SIDS) based on the information,
wherein the risk level includes a low risk, an increased risk, a moderate risk, or a high risk,
wherein the low risk is identified when the infant has a supine sleep position, a normal body temperature, less than about 1% carbon dioxide levels, and normal respiration;
wherein the increased risk is identified when the infant has a) a supine sleep position, a rise of ≥0.5° C. in body temperature, less than about 1% carbon dioxide levels, and normal respiration or b) a supine sleep position or a prone sleep position, a normal body temperature, less than about 1% carbon dioxide levels, and normal respiration;

wherein the moderate risk is identified when the infant has a) a supine sleep position, a normal body temperature, between about 1% to about 3.9% carbon dioxide levels, and normal respiration, b) a supine sleep position, a rise of ≥0.5° C. in body temperature, between about 1% to about 3.9% carbon dioxide levels, and normal respiration, c) a supine sleep position or a prone sleep position, a normal body temperature, between about 1% to about 3.9% carbon dioxide levels, and normal respiration, or d) a supine sleep position or a prone sleep position, a rise of ≥0.5° C. in body temperature, between about 1% to about 3.9% carbon dioxide levels, and normal respiration; and wherein the high risk is identified when the infant has ≥4% carbon dioxide levels.

14. The apparatus of claim 13 wherein the first compartment is separate from the second compartment.

15. The apparatus of claim 13 wherein the housing comprises a connecting arm positioned between the first compartment and the second compartment.

16. The apparatus of claim 13 further comprising a sensor for monitoring an ambient temperature and a sensor for monitoring ambient noise.

17. The apparatus of claim 13 wherein the first compartment sensors have skin contact with the infant for sensing body temperature and breathing sounds.

18. The apparatus of claim 13 wherein the second compartment sensors have exposure to ambient air for sensing the $CO_2$ level from the infant's breathing, and ambient noise and temperature.

19. The apparatus of claim 13, wherein the processing unit is capable of processing the information about the sleep position, the change in the sleep position, the carbon dioxide level, the change in the carbon dioxide level, the temperature, the change in the temperature, the respiration, and the change in the respiration from the plurality of sensors to create an 8-dimensional volumetric space that characterizes the infant's sleep state and performing an individualized algorithm using a Gaussian spheroid on the 8-dimensional volumetric space to determine the SIDS risk level.

* * * * *